United States Patent [19]

Crook

[11] Patent Number: 4,756,904

[45] Date of Patent: Jul. 12, 1988

[54] METHOD OF IMAGING THE HEART USING COPPER-64 CITRATE

[75] Inventor: James E. Crook, Oak Ridge, Tenn.

[73] Assignee: Oak Ridge Associated Universities, Inc., Oak Ridge, Tenn.

[21] Appl. No.: 871,044

[22] Filed: Jun. 5, 1986

[51] Int. Cl.$^4$ .............................................. A61K 49/02
[52] U.S. Cl. ......................................... 424/1.1; 424/9
[58] Field of Search ...................... 424/1.1, 9; 534/10

[56] References Cited

U.S. PATENT DOCUMENTS 3,743,712 7/1973 Gelis ..................................... 424/1.1
3,995,020 11/1976 Dandamundi ........................ 424/1.1
4,036,945 7/1977 Haber .................................... 424/1.1

OTHER PUBLICATIONS

Maziere et al., Int. J. Applied Radiat. Isot., 34(3), pp. 595–601, 1983.
Crook et al., 26th Annual Meeting of the Society of Nuclear Medicine, Clin. Nucl. Med. 10, 1985.
Kirk–Othmer, Encyclopedia of Chemical Technology, vol. 13, p. 238, 1981.

*Primary Examiner*—John F. Terapane
*Assistant Examiner*—John S. Maples
*Attorney, Agent, or Firm*—Luedeka, Hodges & Neely

[57] ABSTRACT

A method of imaging the heart to provide a distinct image using positron emission tomography comprises administering copper-64 citrate and a compatible carrier.

1 Claim, No Drawings

METHOD OF IMAGING THE HEART USING COPPER-64 CITRATE

The invention is a myocardial imaging agent using copper-64 compounds to study the heart and was developed pursuant to a contract with the U.S. Department of Energy.

BACKGROUND OF THE INVENTION

Tissue imaging in the body by introduction of a substance that gives off radiation detected by special imaging cameras is an extremely helpful diagnostic tool in evaluating the state of health of a tissue or organ because it gives researchers a dynamic view of how the body is functioning at a particular location. One such imaging technique, known as positron emission tomography (PET), detects positrons, particles emitted by such radioisotopes as carbon-11, oxygen-15, and nitrogen-13. The disadvantages of using these radioisotopes is their short half-lives, 20.4 minutes for carbon-11, 10 minutes for nitrogen-13, and 2 minutes for oxygen-15, which limit the amount of time there is available from manufacture of the agent until it can be detected. Other considerations made when choosing an appropriate imaging compound include the effectiveness of the uptake of the compound by the particular organ or tissue to be studied, the amount of time the compound is retained in the tissue or organ, the quality of the image obtained, and the ease of making the compound. Therefore there is a continuing need for new imaging agents that are easy to make, sensitive to detection, and have sufficiently long half-lives.

SUMMARY OF THE INVENTION

In view of the above need it is an object of this invention to provide a new myocardial imaging agent.

It is another object of this invention to provide an imaging agent that has high uptake and relatively long retention in the heart.

A third object of this invention is to provide an imaging agent that is sensitive to detection and provides a distinct heart image.

It is a further object of this invention to provide a class of compounds that can be used as heart imaging agents and have relatively long half-lives. Other objects and advantages will become apparent to persons skilled in the art upon study of the specifications and appended claims.

The invention is the new compound copper-64 citrate. It is also an imaging agent comprising a compound that contains the radioisotope copper-64 and a physiologically compatible carrier medium which is suitable for intravenous injection. The preferred compound is a tightly bound salt of copper-64, and the best compound known to inventors is copper-64 citrate although other compounds not yet developed could be as good or better.

DETAILED DESCRIPTION OF THE PREFERRED EMBODIMENT

Copper deficiencies have been shown to cause extensive changes in heart functions such as abnormal connective tissue in major arteries; fibrotic, hypertrophied hearts; and abnormal electrocardiograms in various experimental animals, and it has been hypothesized that copper metabolism may be of prime importance in the causes of ischemic heart disease. Since copper metabolism and cardiac function appear to be closely related, applicants investigated the use of the radioisotope, copper-64, a positron emitter, as a heart imaging agent. An advantage to using copper-64 is its long half-life (12.7 hrs) when compared with carbon-11, nitrogen-13, and oxygen-15. Another advantage that was discovered during the course of the investigation was the unexpectedly distinct image that could be recorded with the PET using the copper-64 isotope in the form of $^{64}$Cu citrate. This high resolution is a definite improvement over other heart imaging agents. Although $^{64}$Cu citrate was used in the following example, other $^{64}$Cu compounds are possible, the preferred compounds being tightly bound $^{64}$Cu salts.

The mechanism of action by which $^{64}$Cu exerts its imaging capabilities is not yet known. However, there is ample evidence to support a number of different mechanisms by which copper could be transported into myocardial cells. Although copper is initially transported as a copper-albumin complex, at the cellular site of transport, copper is transported into cells as a copper-amino acid complex. This particular transport process is operative apparently in the early phase following intravenous copper injections. Another transport process, occurring subsequent to the transport of copper as the amino acid complex, is the formation of a ceruloplasmin-copper complex. Both of the processes are involved in mitochondrial function via providing copper to the mitochondria which is utilized by the mitochondrial cytochrome oxidase enzyme system. Since 30%, by volume, of the myocardial cell is mitochondria, a significant portion of the cell retains the copper isotope, which emits a relatively distinct image in accordance with the concentration of the imaging agent in the area under investigation. Thus, through the mechanisms most likely responsible for its imaging properties, i.e. mitochondrial utilization, $^{64}$Cu citrate may provide a convenient, rapid, and accurate assessment of subcellular organelle function.

The copper-64 compounds can be made by reaction of $^{64}$CuCl$_2$ with a suitable compound to form the desired $^{64}$Cu salt. The $^{64}$Cu can be obtained from suppliers and the techniques for making the desired salts are known to persons of ordinary skill in the art. The compounds are suitable imaging agents for warm blooded animals and are administered using an appropriate administering medium. Determinations of administering media and dosage can be readily determined by persons of ordinary skill in the art.

EXMAPLE

Copper-64, produced by neutron activation of CuO enriched in $^{63}$Cu, was obtained as the chloride in 0.2 M HCl from Oak Ridge National Laboratory, Oak Ridge, Tenn. The specific activity of the $^{64}$Cu chloride solution was approximately 1 mCi/$\mu$g Cu. The $^{64}$Cu was converted to the citrate form by adding Na citrate to appropriate volumes of the radioactive material and neutralizing with 0.2 M NaOH. This solution was filtered through a sterile 0.22$\mu$ micro filter to remove any particulate material. The administered dose of $^{64}$Cu ranged from 0.5 mCi/kg to 1 mCi/kg and the final citrate concentration of the injected solution was 1 mg/kg.

Sixteen closed-chest studies were performed in 6 healthy, adult mongrel dogs of both sexes weighing 15 to 30 kg. The dogs were maintained on a standard laboratory diet which was discontinued 24 hours prior to study. The animals were anesthetized using a combination of xylazine and sodium pentobarbital. Transmission cross-sectional scans of the chest area were performed on each dog with an ECAT II scanner using a $^{68}$Ge ring source with medium resolution filters and standard shadow shields. Measured attenuation coefficients were used for reconstructing the emission tomographs. After the transmission scans were completed, 12-15 mCi of $^{64}$Cu citrate was injected intravenously through an indwelling needle in the hind leg. Serial scans of the heart from base to apex in 10-15 mm steps were made starting 3-5 minutes after injection. After each series was completed, the ECAT II bed was returned to the original position and the dogs were rescanned. This procedure was repeated over a 2 to 4 hour period. Each set of scans required approximately 1 hour for 6 slices, so that 2 to 4 sets of images were obtained in each study. Sequential images were also obtained through a 20-mm section of the heart over a 2-hour period. Additional images from 1 dog were obtained using the new high-resolution ECAT III scanner. Three 15-mm planes were simultaneously recorded through the mid-ventricular and A-V valvular areas of the heart at 5, 25, and 45 minutes after $^{64}$Cu administration. blood clearance curves for $^{64}$Cu citrate were determined in each dog following administration of the compound. The animals were injected through a cannula or catheter in the leg and heparanized venous blood samples were removed from the opposite side. Known aliquots of whole blood, plasma, and erythrocytes were assayed in a well-type scintillation counter to determine the $^{64}$Cu levels present in the different components.

When $^{64}$Cu is administered intravenously it is bound primarily to plasma albumin and transported through the vascular system in this bound form. One set of graphs showed the clearance of $^{64}$Cu from the blood and its concentration in the different blood components in the dog. Within the first 30 minutes after injection, the total $^{64}$Cu in the blood is 10% of the injected dose and < 6% after 1 hour. At this low level, the $^{64}$Cu present in blood causes minimal interference in imaging the myocardium.

One series of scans illustrated representative tomographic images through the heart obtained in a dog using $^{64}$Cu citrate. They showed a rapid and uniform uptake of the compound throughout the myocardium and the characteristic pattern of radioactivity distribution can be seen as tomographic scans are made from the base to the apex of the heart. A second series of scans showed the transmission and reconstructed emission of the transverse section through the left ventricle of the heart. The transmission image outlined the thorax of the dog with the heart shown in the midline. The emission scan showed the left ventricle very distinctly but the right ventricle was less clearly seen because of its thinner wall, lesser blood flow to that portion of the heart, and normalization of the data to the myocardial tissue containing the highest concentration of the $^{64}$Cu citrate. The transaxial cross-sectional images in a final series of scans were made using the ECAT III. The images were obtained simultaneously through 3 sections of the heart and show the typical patterns of the myocardium.

A study of the scans and graphs indicated that the $^{64}$Cu is retained in the heart tissue rather than the blood. To reaffirm this indication, 2 dogs were sacrificed and the hearts were exposed. The cross section corresponding to the image was carefully marked on the surface of the heart using the low power laser beam on the ECAT II. The heart was removed and sliced into 15-mm sections. The sections were photographed and counted in a geometry free counter and it was found that there was a concentration of the $^{64}$Cu in the heart tissue. Although the myocardial tissue concentration is not as high as those reported using $^{201}$Tl, $^{52}$Mn, or $^{81}$Rb, sufficiently high ratios of heart to blood and other surrounding tissues necessary for imaging were obtained as evidenced by the excellent images obtained from the ECAT II and III scans.

The primary significance of this invention is that the isotope being imaged concentrates in the organ being examined. Results indicate that the uptake of $^{64}$Cu citrate by myocardial tissue occurs quite rapidly and remains constant over the time periods studied. The $^{64}$Cu citrate is present in blood at low concentrations and would contribute in a very minimal way to the images obtained. It is likely that $^{64}$Cu concentrates in other locations of the body in addition to the heart. It is known that not only do certain components that make up the arterial wall bind to copper but also an enzyme present in the arterial wall needs copper to function. Therefore, it is likely that $^{64}$Cu compounds would be useful to study arterial walls. This activity of copper might well extend to the veins thereby making $^{64}$Cu an appropriate radionuclide for the study of vascular disease.

Unlike other positron-emitting agents that are in current use or that have been proposed as myocardial-imaging agents, $^{64}$Cu is easily prepared and requires a minimal amount of pre-injection preparation. Like other successfully employed compounds containing short-lived radionuclides, relatively long-lived $^{64}$Cu has the ability to provide images with the distinct structures of the heart clearly demarcated. It is concentrated in myocardium and remains in the organ for a sufficient length of time to insure maximal imaging time periods.

The central issue of the present investigation was the utility of copper-64 in imaging myocardial tissue. From the results obtained, it is evident that copper-64 citrate yields useful images of the myocardium. In support of its consideration for future use as a cardiac imaging agent is its ease of preparation, high affinity for myocardium, and its long half-life which can provide access to positron-emitting radionuclides to centers without cyclotron facilities.

I claim:

1. A method of imaging the heart comprising administering intravenously an effective amount of radioactive copper-64 cirtrate and a physiologically compatible carrier medium.

* * * * *